United States Patent [19]

Schnurr et al.

[11] Patent Number: 5,783,711
[45] Date of Patent: Jul. 21, 1998

[54] PROCESS FOR THE PREPARATION OF HETEROCYCLIC ALDEHYDES

[75] Inventors: Werner Schnurr, Herxheim; Rolf Fischer, Heidelberg; Joachim Wulff-Döring, Frankenthal; Matthias Irgang, Heidelberg; Horst Neuhauser, Dudenhofen, all of Germany

[73] Assignee: BASF Aktiengesellschaft, Ludwigshafen, Germany

[21] Appl. No.: 750,121

[22] PCT Filed: May 31, 1995

[86] PCT No.: PCT/EP95/02071

§ 371 Date: Feb. 20, 1997

§ 102(e) Date: Feb. 20, 1997

[87] PCT Pub. No.: WO95/33741

PCT Pub. Date: Dec. 14, 1995

[30] Foreign Application Priority Data

Jun. 3, 1994 [DE] Germany .......................... 44 19 514.1

[51] Int. Cl.⁶ .......................... C07D 315/00; C07D 307/02
[52] U.S. Cl. .......................... 549/425; 549/346; 549/483
[58] Field of Search .................. 549/425, 346, 549/483

[56] References Cited

FOREIGN PATENT DOCUMENTS

| | | |
|---|---|---|
| 343 640 | 11/1989 | European Pat. Off. |
| 439 115 | 7/1991 | European Pat. Off. |
| 546 396 | 6/1993 | European Pat. Off. |
| 40 39 918 | 12/1990 | Germany |

*Primary Examiner*—Amelia Owens
*Attorney, Agent, or Firm*—Keil & Weinkauf

[57] ABSTRACT

Preparation of heterocyclic aldehydes I

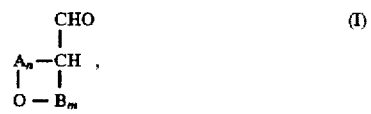

(A, B=optionally substituted methylene groups; $m$, $n$=1 to 5; $m+n>2$), by hydrogenation of carboxylic acids IIa

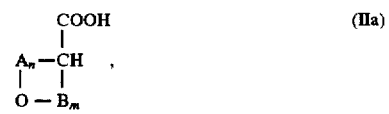

or one of their esters II*b* derived from a $C_1$–$C_{10}$ alcohol, at a temperature of from 200° to 450° C. over a catalyst.

The end products are suitable as intermediates for herbicides of the cyclohexanone class.

10 Claims, No Drawings

PROCESS FOR THE PREPARATION OF HETEROCYCLIC ALDEHYDES

DESCRIPTION

The present invention relates to a process for the preparation of aldehydes of the general formula I

in which the variables A and B stand for methyl groups which may carry one or two substituents inert under the conditions of the reaction, and $m$ and $n$ stand for 1 to 5, the sum of $m$ and $n$ being greater than 2.

Aldehydes of the general formula I, in which the formyl group is attached to a saturated ring interrupted by an oxygen atom, are of great significance as intermediates. Thus 4-formyltetrahydropyran is for example a building block for herbicides of the cyclohexenone class (cf EP-A 142,741).

The preparation of aldehydes from carboxylic acids or carboxylic acid esters is usually carried out in industrial plants in two stages in which the starting materials are first of all reduced as far as the alcohol stage, and oxidation is then performed to form the aldehyde. For example, the preparation of 4-formyltetrahydropyran from methyl tetrahydropyran-4-carboxylate has been well examined (cf EP-A 546,396 and DE-A 4,039,918).

EP-A 439,115 discloses the hydrogenation of aliphatic or alicyclic carboxylic acids, eg, cyclohexanoic acid, in the presence of a chromium/zirconium dioxide catalyst to produce the corresponding aldehydes.

EP-A 343,640 describes the hydrogenation of heteroaromatic carboxylic acids to the corresponding aldehydes where the catalyst used must contain at least one zinc or yttrium oxide, an oxide of the Lanthanide Group, or an oxide of a Group IVa element such as zirconium oxide. No reference is made to saturated heterocyclics.

It is the object of the invention to partially hydrogenate the carboxylic acids IIa or the esters IIb by a direct route to form the aldehydes I, ie without detouring through the alcohols and subsequent oxidation to the aldehydes Accordingly, there has been found a process for the preparation of the heterocyclic aldehydes of formula I, wherein a carboxylic acid of the general formula IIa

or one of its esters IIb derived from a $C_1$–$C_{10}$ alcohol, is hydrogenated at a temperature of from 200° to 450°C. over a catalyst.

The carboxylic acids IIa and esters IIb suitable for the reaction to be carried out in the process of the invention can carry, on the ring, primarily from one to three substituents (R) which are inert under the reaction conditions, in particular $C_1$–$C_3$ alkyl or $C_1$–$C_3$ alkoxy groups.

The preferred end products of the process I are, for example, those derived from carboxylic acids IIa or their esters IIb, in which the ring containing the oxygen atom exhibits from 5 to 7 ring members, ie in which the sum of $n$ and $m$ is from 3 to 5, whilst one or two of the radicals R stand(s) for a $C_1$–$C_3$ alkyl group and the other radicals R stand for hydrogen. Such compounds I are primarily 3-formyl-2-methyltetrahydrofuran, 3-formyl-2,4-dimethyltetrahydrofuran, 2-ethyl-4-formyl-tetrahydrofuran, 3-formyl-5-isopropyltetrahydropyran, and 3-formyl-2,7-dimethyl-oxepane. Those end products I are particularly preferred in which the hetero ring is unsubstituted, as in 3-formyltetrahydrofuran and, in particular, 4-formyltetrahydropyran.

In the group of esters regarded as being suitable starting materials it is preferred to use those esters IIb which are derived from $C_1$–$C_{10}$ monoalcohols. Of these, those esters IIb are primarily suitable in which the monoalcohol component exhibits an unsubstituted $C_1$–$C_{10}$ hydrocarbon radical, as in the case of the very particularly preferred $C_1$–$C_{10}$ alkanols, preferably $C_1$–$C_{10}$ alkanols such as, primarily, methanol, ethanol, n-propanol, 1-methylethanol, n-butanol, 1-methylpropanol, 2-methylpropanol and 1,1-dimethylethanol and in addition n-pentanol, n-hexanol, n-heptanol, n-octanol, and 2-ethylhexanol, and also $C_3$–$C_{10}$-cycloalkanols, preferably $C_3$–$C_8$ cycloalkanols such as, primarily, cyclopentanol and cyclohexanol and also 2-methylcyclohexanol, 2,6-dimethylcyclohexanol, cycloheptanol, and cyclooctanol, $C_6$–$C_{10}$ aromatic monoalcohols, preferably phenol and also the naphthols or $C_7$–$C_{10}$ aralkanols, preferably phenyl-($C_1$–$C_3$)-alkanols such as, primarily, phenylmethanol, 2-phenylethanol and 3-phenylpropan-1-ol and also 1-phenylethanol, 2-phenylpropan-1-ol, and 1-phenylpropan-1-ol.

In the case of the preparation of 4-formyltetrahydropyran it is particularly preferred to start from tetrahydropyran-4-carboxylic acid or its methyl or ethyl ester.

Some of the carboxylic acids IIa and esters IIb are commercially available, or they can be obtained in known manner (cf Houben-Weyl, *Methoden der Organischen Chemie* 4th Edition, Thieme Verlag, Stuttgart, Vol. 8, page 365 et seq and page 508 et seq).

The catalysts suitable for the process of the invention preferably consist of from 75 to 100 wt %, and more preferably of from 90 to 100 wt %, of zirconium dioxide and/or one or a number of manganese oxides. The zirconium dioxide used usually has a BET surface area of from 5 to 150, preferably from 20 to 130, and in particular from 40 to 120 m$^2$/g, where the BET surface area is taken to be the catalyst surface area as determined by the Brunauer-Emmett-Teller method (cf Z. Anal. Chem. 238, page 187 (1968)). Preferably monoclinic zirconium dioxide is used and also that having a cubic or tetragonal crystal lattice.

Of the manganese oxides, manganese(II) oxide and also manganese(III) oxide and manganese(IV) oxide and mixtures thereof are primarily suitable. The BET surface areas range in this case usually from 5 to 60 m$^2$/g and preferably from 10 to 50 m$^2$/g.

In a preferred embodiment of the process of the invention there is used a catalyst which contains, in addition to zirconium dioxide and/or one or more manganese oxides, from 0.1 to 10 and primarily from 0.5 to 5 wt % of one or more compounds of chromium, yttrium, and/or one or more elements of the lanthanide series of the Periodic Table (referred to below as "lanthanide elements"), the compounds of the lanthanide elements being preferred.

The lanthanide elements comprise lanthanum, cerium, praseodymium, neodymium, promethium, samarium, europium, gadolinium, terbium, dysprosium, holmium, erbium, thullium, ytterbium and lutetium.

The compounds of lanthanum and praseodymium, and in addition those of cerium, samarium, neodymium, and europium, are primarily suitable as constituents of the catalysts used in the present invention.

Those catalysts are preferably used in which the chromium or the lanthanide elements is/are present at least partially, and in particular to an extent of more than 80 wt %, in oxidic form.

In the preparation of the catalysts these elements are therefore preferably used as oxides, or in the form of those of their compounds which can be readily converted to the oxides by heating, if required in the presence of water and/or oxygen.

These include, in the case of the lanthanide elements, primarily the trivalent oxides such as cerium(III) oxide and lanthanum(III) oxide and also the chlorides and nitrates such as lanthanum(III) nitrate, cerium(III) nitrate, praseodymium (III) chloride and samarium(III) chloride and compounds containing organic anions such as the acetates and the oxalates, eg cerium(III) oxalate.

In the case of chromium, chromium(III) oxide and the chlorides, nitrates and acetates of trivalent chromium, in particular chromium(III) chloride and chromium(III) nitrate, are primarily suitable for the preparation of the catalysts suitable for the process of the invention.

In a particularly preferred embodiment of the process of the invention a catalyst is used which essentially consists of zirconium dioxide and contains from 0.1 to 10, in particular from 0.5 to 5 wt % of a compound of one or more lanthanide elements, primarily lanthanum(III) oxide.

Incidentally, traces of the elements iron, aluminum, silicon and magnesium at a total concentration of less than 2 wt %, based on the total weight of the catalyst, have no visibly injurious effect on the success of the process of the invention.

These catalysts, if not commercially available, can be obtained in known manner (cf, eg, Catal. Rev. - Sci. Eng. 27, pp 341 to 372 (1985)).

The catalysts can be used as supported catalysts on a conventional inert support such as silicon dioxide or aluminum oxide or, primarily, as solid catalysts. They are suitable in the form of extrudates preferably having a maximum diameter of from 1 to 5 mm, pellets or balls.

The amounts stated below concerning the composition of the catalysts relate to their active material with no regard to the support materials.

The hydrogenation of the carboxylic acids IIa or esters IIb is carried out preferably at temperatures of from 250° to 400° C., usually from 300° to 380° C. and pressures of from 0.1 to 20 bar, preferably from 0.8 to 5 bar and in particular under standard pressure.

Generally, the process is carried out at a space velocity of from 0.01 to 10 kg, preferably from 0.01 to 3 kg, of starting compound II per kilogram of catalyst per hour.

Preferably the conditions are adjusted such that during the hydrogenation from 2 to 100 mol, in particular from 10 to 70 mol, of hydrogen are present per mole of II.

As a precautionary measure, an inert gas, primarily nitrogen or steam and also argon can be mixed with the hydrogen.

Particularly the solid compounds II can be caused to react in liquid phase in a solvent which is inert under the hydrogenating conditions, such as a hydrocarbon, eg, n-hexane or cyclohexane, or water, but the reaction is preferably carried out without the use of a solvent.

In reactions in the gas phase the compounds II are introduced into the reaction zone advantageously in vaporous form and, if required, by means of a stream of carrier gas. The preferred carrier gas is nitrogen.

Preferably the hydrogenation of the compounds II is carried out continuously and primarily in the gas phase following the techniques known for this purpose, in particular over a fixed catalyst bed.

In a further preferred embodiment, which is in itself particularly advantageous, the starting material used for the preparation of 4-formyltetrahydropyran is tetrahydropyran-4-carboxylic acid or one of its esters derived from a $C_1$–$C_{10}$ alcohol, and the hydrogenation is carried out in the presence of a catalyst which essentially consists of zirconium dioxide and contains from 0.1 to 5 wt % of lanthanum(III) oxide, in which case the process is advantageously carried out at a temperature of from 300° to 380° C. and a pressure of from 0.8 to 5 bar.

Processing of the crude reaction mixture to provide the end product I can be carried out in known manner, primarily by removal, if required, of the solvent by distillation and purification of the crude product, for example by distillation or recrystallization.

The catalysts can in most cases be regenerated by heating to from 300° to 450° C. in a stream of oxygen or air.

During the hydrogenation of the carboxylic acids IIa or the esters IIb by-products are formed in some cases to a minor extent, as a result of overreduction, especially the corresponding primary alcohols, which can be oxidized in known manner, if desired, to produce the aldehydes I.

Since oxidation of these alcohols is also successfully carried out using the catalysts described above as being suitable for use in the process of the invention, it is possible to recycle the said alcohols to the process of the invention, advantageously after mixing the same with starting material IIa or IIb.

In some cases the primary alcohols react with the carboxylic acids IIa to form esters or with the esters IIb to form transesterification products, which can be converted to aldehydes I in the process of the invention by causing them to be recycled to the process, advantageously after being mixed with fresh carboxylic acid IIa or ester IIb.

For example, in the synthesis of 4-formyltetrahydropyran, the by-products {4-hydroxymethyltetrahydropyran and tetrahydropyran-4-yl-methyl tetrahydropyran-4-carboxylate} can be recycled to the process of the invention together with unconverted starting compound {tetrahydropyran-4-carboxylic ester (IIb)} without previous separation, since the said components have a higher boiling point than the desired end product 4-formyltetrahydropyran and the latter is thus readily separable.

The process of the invention gives yields of the aldehydes I usually between 20 and 80%, in selectivities of from 50 to 90%.

The end products are suitable as intermediates for herbicides of the cyclohexenone class (cf. eg, EP-A 142,741).

EXAMPLES

In the following examples some of the catalysts used were commercially available, whereas the others we prepared ourselves.

A) Preparation Of The Catalysts

Monoclinic zirconium dioxide (Norton, Akron, Ohio) in the form of extrudates (3 mm in diameter) or manganese oxide (MnO, prepared from manganese(II) carbonate, cf Hollemann-Wiberg, Lehrbuch der anorganischen Chemie, 81st–90th Edition, Verlag Walter de Gruyter, Berlin, page 905) in the form of pellets was impregnated with an aqueous solution of the lanthanide element nitrate, of yttrium(III) nitrate, or of chromium(III) nitrate with thorough mixing and kept at room temperature for 2 hours. The catalyst thus obtained was then dried for 15 hours at a temperature of 120° C. and heated for 2 to 4 hours at from 400° to 500° C. in a stream of air.

B) Preparation Of 4-Formyltetrahydropyran

Per hour, 10 grams of methyl tetrahydropyran-4-carboxylate were evaporated at a temperature of from 250° to 300° C., and caused to react, together with 100 liters of hydrogen, in a tubular reactor having a diameter of 25 mm over 100 g of catalyst CAT doped as stated and having the surface area S stated at a temperature of T°C. The continuously withdrawn crude product was condensed and analyzed by quantitative gas chromatography for 4-formyltetrahydropyran.

The details of the experiments carried out and the results thereof are summarized in the following table.

Purification by distillation:

| | | |
|---|---|---|
| - Fraction 1: methanol + low-boilers | (b.p. 38–80° C./300 mbar) | 2.5 kg |
| - Fraction 2: FTHP | (b.p. 81° C./30 mbar) | 8.0 kg (70 mol) |
| - Fraction 3: THPE | (b.p. 94° C./30 mbar) | 1.0 kg (7 mol) |
| - Fraction 4: HMTHP | (b.p. 118° C./30 mbar) | 6.8 kg (59 mol) |
| - Fraction 5: THPPE | (b.p. 165° C./5 mbar) | 2.1 kg (9 mol) |

Intermediate fractions were reused in the next distillation and residual useful products thus recovered. The yield of 4-formyltetrahydropyran (based on fresh THPE) was, following distillation, 90% (purity better than 99%).

TABLE

Preparation Of 4-Formyltetrahydropyran

| No. | CAT | Doped with | Doping concentration [wt %] | S [m²/g] | T °C. | 4-Formyltetrahydropyran Conversion [%] | Yield [%] | Selectivity [%] |
|---|---|---|---|---|---|---|---|---|
| 1 | $ZrO_2$ | — | — | 42 | 350 | 62.5 | 39.3 | 62.8 |
| 2 | $ZrO_2$ | La | 3 | 51 | 330 | 48.9 | 39.7 | 81.2 |
| 3 | $ZrO_2$ | La | 3 | 96 | 330 | 51.9 | 37.2 | 71.7 |
| 4 | $ZrO_2$ | La | 3 | 51 | 350 | 68.7 | 50.5 | 73.5 |
| 5 | $ZrO_2$ | Ce | 3 | 51 | 350 | 50.0 | 36.1 | 72.2 |
| 6 | $ZrO_2$ | Pr | 3 | 51 | 350 | 65.7 | 47.8 | 72.8 |
| 7* | $ZrO_2$ | La | 3 | 96 | 350 | 100 | 76.0 | 76.0 |
| 8 | $ZrO_2$ | Y | 3 | 92 | 330 | 54 | 37.1 | 68.7 |
| 9 | MnO | — | — | 44 | 370 | 57.3 | 36.1 | 63.0 |

*Starting compound: tetrahydropyran-4-carboxylic acid

C) Preparation Of 4-Formyltetrahydropyran in a Pilot Plant

Per hour, 130 grams of methyl tetrahydropyran-4-carboxylate were evaporated at a temperature of 250° C., and caused to react, together with 1200 liters of hydrogen, in a tubular reactor having a diameter of 24 mm and a length of 4 m over 1700 mL of catalyst 2 at a temperature of from 330° C. to 355° C. The continuously withdrawn crude product was condensed and analyzed by quantitative gas chromatography. The duration of the experiment was 2700 h. The average aldehyde yield was 52% (selectivity 83%).

D) Preparation of 4-Formyltetrahydropyran (FTHP) in a Pilot Plant with Recycling of the By-products The method used was that described under C) except that the continuously withdrawn crude product following condensation was collected over a period of 7 days and then distilled batchwise (5 m Sulzer CY Packing, approx. 50 theoretical separating stages). Following said purification by distillation, unconverted methyl tetrahydropyran-4-carboxylate (THPE), 4-hydroxymethyltetrahydropyran (HMTHP), and tetrahydropyranmethyl tetrahydropyran-4-carboxylate (THPPE) were recycled to the hydrogenation stage. After a number of recycles had been carried out the following steady-state quantities were established:

Feed (21.8 kg every 7 days):

| | |
|---|---|
| - THPE (fresh) | 11.3 kg (78 mol) |
| - THPE (recycled) | 1.0 kg (7 mol) |
| - HMTHP (recycled) | 6.7 kg (58 mol) |
| - THPPE (recycled) | 2.1 kg (9 mol) |
| - Other by-products | 0.7 kg. |

We claim:

1. A process for the preparation of an aldehyde of the general formula I

in which the variables A and B stand for methylene groups which may carry one or two substituents inert under the reaction conditions, and $\underline{m}$ and $\underline{n}$ stand for 1 to 5, the sum of $\underline{m}$ and $\underline{n}$ being greater than 2, wherein a carboxylic acid of the general formula IIa

or one of its esters IIb derived from a $C_1$–$C_{10}$ alcohol, is hydrogenated at a temperature of from 200° to 450° C. over a catalyst.

2. A process as defined in claim 1, wherein the hydrogenation is carried out in the gas phase.

3. A process as defined in claim 1, wherein the catalyst substantially consists of zirconium dioxide and/or one or more manganese oxides.

4. A process as defined in claim 1, wherein a catalyst is used which contains from 0.1 to 10 wt % of one or more compounds of chromium and/or of one or more elements of the lanthanide series of the Periodic Table.

5. A process as defined in claim 4, wherein the compounds of chromium and/or of the elements of the lanthanide series of the Periodic Table are present in the catalyst at least partially in oxidic form.

6. A process as defined in claim 1, wherein a catalyst is used which essentially consists of zirconium dioxide and from 0.1 to 10 wt % of a compound of one or more elements of the lanthanide series of the Periodic Table.

7. A process as defined in claim 1, wherein a catalyst is used which essentially consists of zirconium dioxide and contains from 0.5 to 5 wt % of lanthanum(III) oxide.

8. A process as defined in claim 1, wherein monoclinic zirconium dioxide is used.

9. A process for the preparation of 4-formyltetrahydropyran, wherein tetrahydropyran-4-carboxylic acid or one of its esters derived from a $C_1$-$C_{10}$ alcohol is hydrogenated in the presence of a catalyst, which essentially consists of zirconium dioxide and contains from 0.1 to 5 wt % of lanthanum(III) oxide.

10. A process as defined in claim 1, wherein the desired product (I) is then separated from the hydrogenation mixture and the by-products comprising the alcohol corresponding to the aldehyde (I) and/or esters of said alcohol with IIa or IIb, are again treated by said process, if desired together with starting compound IIa or IIb.

* * * * *

UNITED STATES PATENT AND TRADEMARK OFFICE
CERTIFICATE OF CORRECTION

PATENT NO.: 5,783,711            Page 1 of 3

DATED: July 21, 1998

INVENTOR(S): SCHNURR et al.

It is certified that error appears in the above-identified patent and that said Letters Patent is hereby corrected as shown below:

Col. 6, claim 1, line 36, delete "general";
    line 43 delete "in which the variables" and substitute --where--;
        delete "stand for" and substitute --are--;
    line 44, after "substituents" insert --that are--;
    line 45, delete "stand for" and substitute --are--;
    line 47, delete "general";
    line 52, delete "one of its esters" and substitute --an ester--;
    line 52, after "from" insert --a carboxylic acid of the formula IIa and--;
    line 53, delete "over" and substitute --in the presence of--.

Col. 6, line 55, delete "A process as" and substitute --The process--

Col. 6, line 57, delete "A process as" and substitute --The process--
    line 58, delete "substantially"; after "consists" insert --essentially--;
        delete "and/or" and substitute --or--;
    line 59, after "oxides" insert --or a mixture of zirconium dioxide and one or more manganese oxides--.

Col. 6, claim 4, line 60, delete "A process as" and substitute --The process--;
        delete "a" and substitute --the--;
    line 61, delete "is used which"; delete "wt%" and substitute --% by weight--;
    line 62, delete "and/or" and substitute --or--;
    line 63, after "Table" insert --or a mixture of one or more compounds of chromium and one or more elements of the lanthanide series of the Periodic Table--.

UNITED STATES PATENT AND TRADEMARK OFFICE
CERTIFICATE OF CORRECTION

PATENT NO.: 5,783,711

DATED: July 21, 1998

INVENTOR(S): SCHNURR et al.

It is certified that error appears in the above-identified patent and that said Letters Patent is hereby corrected as shown below:

Col. 6, claim 5, line 64, delete "A process as" and substitute --The process--;
    line 65, delete "and/or" and substitute --or--;
    line 65, after "Table" insert --or the compounds of chromium and the elements of the lanthanide series of the Periodic Table--;
    line 66, delete "present in the catalyst".

Col. 7, claim 6, line 1, delete "A process as" and substitute --The process--;
    line 1, delete "a" and substitute --the--;
    line 2, delete "is used which essentially"; after "consists" insert --essentially--;
    line 3, delete "wt%" and substitute --% by weight--.

Col. 7, claim 7, line 5, delete "A process as" and substitute --The process--;
    line 5, delete "a" and substitute --the--; delete "is";
    line 6, delete "used which essentially"; after "consists" insert --essentially--;
    line 7, delete "contains"; delete "wt%" and substitute --% by weight--.

Col. 7, claim 8, line 8, delete "A process as" and substitute --The process--;
line 8, after "wherein" insert ---the catalyst is---; line 9, delete ---is---
    Col. 8, claim 9, line 1 bridging line 2, delete "which essentially consists" and substitute --said catalyst consisting essentially--;
    line 2, delete "contains";
    line 3, delete "wt%" and substitute % by weight--.

Col. 8, claim 10, line 4, delete "A process as" and substitute --The process--;
    line 5 bridging line 6, delete "wherein the desired product (I) is then separated" and substitute --further comprising separating the aldehyde of the formula I--;
    line 6, after "and" insert --subjecting--;
    line 9, delete "are again treated by said process" and "together with";
    line 10, delete "starting" and substitute --in the presence of a--;

UNITED STATES PATENT AND TRADEMARK OFFICE
CERTIFICATE OF CORRECTION

PATENT NO. : 5,783,711
DATED : July 21, 1998
INVENTOR(S) : SCHNURR et al.

It is certified that error appears in the above-identified patent and that said Letters Patent is hereby corrected as shown below:

line 10, after "IIb" insert --, to the hydrogenation process--.

Signed and Sealed this

Seventh Day of September, 1999

Attest:

Q. TODD DICKINSON

Attesting Officer

Acting Commissioner of Patents and Trademarks